United States Patent
Huth et al.

[11] Patent Number: 6,136,805
[45] Date of Patent: Oct. 24, 2000

[54] QUINOXALINE DIONE DERIVATIVES, THEIR PRODUCTION AND THEIR USE IN MEDICAMENTS

[75] Inventors: Andreas Huth; Martin Krüger; Eckhard Ottow; Dieter Seidelmann; Roland Neuhaus; Herbert Schneider; Lechoslaw Turski, all of Berlin, Germany

[73] Assignee: Scnering Aktiengesellschaft, Germany

[21] Appl. No.: 08/952,520

[22] PCT Filed: May 23, 1996

[86] PCT No.: PCT/DE96/00948

§ 371 Date: Nov. 21, 1997

§ 102(e) Date: Nov. 21, 1997

[87] PCT Pub. No.: WO96/37500

PCT Pub. Date: Nov. 28, 1996

[30] Foreign Application Priority Data

May 24, 1995 [DE] Germany .......................... 195 19 979

[51] Int. Cl.[7] ........................ A61K 31/498; C07D 241/44
[52] U.S. Cl. ............................ 514/249; 514/81; 544/337; 544/354
[58] Field of Search ..................... 544/354, 337; 514/81, 249

[56] References Cited

U.S. PATENT DOCUMENTS 5,166,155  11/1992  Jorgensen et al. ....................... 514/249

FOREIGN PATENT DOCUMENTS

| 2253846 | 9/1992 | United Kingdom . |
| 94/25469 | 11/1994 | WIPO . |
| 96/10023 | 4/1996 | WIPO . |
| 96/12724 | 5/1996 | WIPO . |
| 96/12725 | 5/1996 | WIPO . |

OTHER PUBLICATIONS

Epperson et al, Bioorganic & Medicinal Chemistry Letters, vol.3,p.2801–2804, 1993.
Francis et al.,Journal of Neurochemistry,vol.60, p. 1589–1604, 1993.
McBurney,Neurobiology of Aging,vol.15,p.271–273, 1994.

*Primary Examiner*—Richard L. Raymond
*Attorney, Agent, or Firm*—Millen, White, Zelano & Branigan, P.C.

[57] ABSTRACT

Quinoxalinedione derivatives of formula (I)

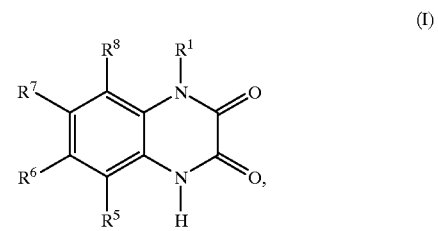

are described, and their use in pharmaceutical agents.

8 Claims, No Drawings

QUINOXALINE DIONE DERIVATIVES, THEIR PRODUCTION AND THEIR USE IN MEDICAMENTS

This application is a 371 of PCT/DE96/00948, filed May 23, 1996.

The invention relates to quinoxalinedione derivatives, their production and use in pharmaceutical agents.

It is known that quinoxaline derivatives have an affinity to the quisqualate receptors and, because of the affinity, are suitable as pharmaceutical agents for the treatment of diseases of the central nervous system.

The compounds according to the invention have formula I

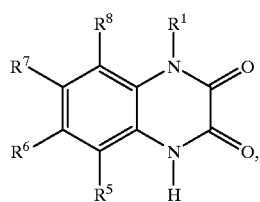

in which $R^1$ means —$(CH_2)_n$—$CR^2H$—$(CH_2)_m$—Z and $R^5$, $R^6$, $R^7$ and $R^8$ are the same or different and mean hydrogen, $C_{1-6}$ alkyl, in which optionally one or more hydrogen atoms are replaced by halogen atoms, nitro, halogen, $NR^9R^{10}$, cyano, $SO_pR^{11}$, $SO_2NR^{12}R^{13}$, $SO_3H$, $SO_3C_{1-6}$ alkyl or $OR^{14}$ whereby $R^2$ means hydrogen or —$(CH_2)_q$—$R^3$, $R^3$ means hydrogen, hydroxy, $C_{1-6}$ alkoxy or $NR^{15}R^{16}$, n, m or q each mean 0, 1, 2 or 3, Z means POXY, OPOXY, $SO_2R^{17}$, $COR^{18}$, halogen, cyano or tetrazole, $R^{11}$ means H, $C_{1-6}$ alkyl, phenyl, p means 0, 1 or 2, $R^{12}$ and $R^{13}$, independently or one another, mean hydrogen or $C_{1-4}$ alkyl, $R^{14}$ means A—$R^{19}$ or a $C_{6-12}$ aryl or hetaryl radical, which can be substituted with halogen, $C_{1-6}$ alkoxy, hydroxy, cyano, $NR^{20}R^{21}$, $C_{1-6}$ alkyl optionally substituted with halogen and/or $COR^{22}$, and A means straight-chain or branched, saturated or unsaturated alkylene with $C_{1-20}$ carbon atoms, in which one or more carbon atoms can be replaced by O, S and/or $NR^{26}$ and which can be substituted in one or more places with halogen, and $R^{19}$ means hydrogen, $NR^{24}R^{25}$, halogen, $C_{1-6}$ alkyl, which optionally is substituted in several places with halogen, $C_{1-6}$ alkoxy, $COR^{23}$, CN or a $C_{6-12}$ aryl or hetaryl radical, which can be substituted with halogen, $C_{1-6}$ alkoxy, hydroxy, cyano, $NR^{20}R^{21}$, $C_{1-6}$ alkyl, which can be substituted with halogen, and/or $COR^{22}$, and $R^{18}$ means hydrogen, $C_{1-4}$ alkyl, hydroxy, $C_{1-6}$ alkoxy or $NR^{27}R^{28}$, $R^{17}$, $R^{22}$ and $R^{23}$ mean hydroxy, $C_{1-6}$ alkoxy or $NR^{29}R^{30}$, $R^{26}$ means hydrogen, $C_{1-6}$ alkyl, $C_{1-6}$ alkanoyl, X and Y are the same or different and mean hydroxy, $C_{1-6}$ alkoxy, $C_{1-4}$ alkyl or $NR^{27}R^{28}$, $R^9$ $R^{10}$, $R^{20}$ and $R^{21}$ and/or $R^{25}$ and $R^{24}$ are the same or different and mean hydrogen, CO—$C_{1-6}$ alkyl, phenyl or $C_{1-6}$ alkyl, which can optionally be substituted with $C_{1-4}$ alkoxy or an amino group optionally mono- or disubstituted with $C_{1-4}$ alkyl, or together with the nitrogen atom form a 5- or 7-membered saturated heterocycle that can contain another N, S or O atom and can be substituted or form an unsaturated 5-membered heterocycle that can contain 1–3 N atoms and can be substituted, $R^{15}$ and $R^{16}$, $R^{27}$ and $R^{28}$, $R^{29}$ and $R^{30}$ are the same or different and mean hydrogen, $C_{1-4}$ alkyl, phenyl or together with the nitrogen atom form a 5- or 7-membered saturated heterocycle that can contain another oxygen, sulfur or nitrogen atom and can be substituted or form an unsaturated 5-membered heterocycle that can contain 1–3 N atoms and can be substituted, whereby one of radicals $R^5$–$R^8$ always means $OR^{14}$, and $R^{14}$ does not mean H or $C_{1-6}$ alkyl optionally substituted in 1–3 places with halogens.

The compounds of general formula I also contain the possible tautomeric forms and comprise the E or Z isomers or, if a chiral center is present, the racemates or enantiomers.

The substituents are preferably in 6- and/or 7-position.

Alkyl is defined respectively as a straight-chain or branched alkyl radical, such as, for example, methyl, ethyl, propyl, isopropyl, butyl, isobutyl, sec-butyl, pentyl, isopentyl, hexyl.

Halogen is defined respectively as fluorine, chlorine, bromine and iodine, especially fluorine, chlorine and bromine.

As aryl radicals $R^{14}$ and $R^{19}$, for example, naphthyl, biphenylyl and especially phenyl can be mentioned.

Hetaryl radicals $R^{14}$ and $R^{19}$ are 5- to 6-membered and can contain 1–3 heteroatoms, such as N, O and/or S atoms, such as for example, thiophene, furan, pyrrole, imidazole, oxazole, thiazole, triazole, pyridine, pyrazine, pyrimidine and pyridazine.

If A means a straight-chain or branched alkylene group, the latter contains especially 1–8 carbon atoms, whereby 1–3 C atoms can be replaced by O, S and/or $NR^{26}$; there can be mentioned, for example: methylene, ethylene, propylene, isopropylene, butylene, isobutylene, 3-oxapropylene, 3-thiapentylene, 3-oxapentylene, 3-(N-methyl)-azapentylene, 4-oxapentylene, 4-oxa-hept-6-en-yl, 2-methyl-3-oxapentylene, 3,6-dioxaheptylene, 3-oxa-6-thiaoctylene, 3,6-dioxaoctylene.

If $R^9$ and $R^{10}$, $R^{15}$ and $R^{16}$, $R^{27}$ and $R^{28}$, $R^{24}$ and $R^{25}$, $R^{20}$ and $R^{21}$, $R^{29}$ and $R^{30}$ together with the nitrogen atom form a saturated heterocycle, then, for example, piperidine, pyrrolidine, morpholine, thiomorpholine, hexahydroazepine or piperazine is meant. The heterocycle can be substituted in one to three places with $C_{1-4}$ alkyl or a phenyl, benzyl or benzoyl radical optionally substituted with halogen. For example, N-methyl-piperazine, 2,6-dimethylmorpholine, phenylpiperazine or 4(4-fluorobenzoyl-piperidine can be mentioned.

As unsaturated alkenylene group A, alkenyl and alkinyl are suitable, such as, for example, 2-propenylene, 2-butenylene, and 2-propinylene.

If $R^9$ and $R^{10}$, $R^{15}$ and $R^{16}$, $R^{27}$ and $R^{28}$, $R^{24}$ and $R^{25}$, $R^{20}$ and $R^{21}$, $R^{29}$ and $R^{30}$ together with the nitrogen atom form an unsaturated heterocycle, then, for example, imidazole, pyrazole, pyrrole and triazole can be mentioned, which can be substituted in one to two places with cyano, $C_{1-4}$ alkyl, phenyl or $CO_2C_{1-6}$ alkyl.

As a preferred embodiment, there can be mentioned: $R^5$, $R^6$, $R^7$ and $R^8$, which can be the same or different, mean hydrogen, $C_{1-6}$ alkyl, in which optionally one or more hydrogen atoms are replaced by halogen atoms, nitro, cyano or $OR^{14}$; $R^3$ means hydrogen, and Z means POXY or $COR^{18}$.

If an acid function is contained, the physiologically compatible salts of organic and inorganic bases are suitable as salts, such as, for example, the readily soluble alkali and alkaline-earth salts, as well as N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropanediol, Sovak base, 1-amino-2,3,4-butanetriol.

If a basic function is contained, the physiologically compatible salts of organic and inorganic acids are suitable, such as HCl, $H_2SO_4$, phosphoric acid, citric acid, tartaric acid, etc.

Preferred are phosphonic acid and carboxylic acid derivatives, which can be substituted in one to two places.

The compounds of formula I as well as their physiologically compatible salts can be used as pharmaceutical agents because of their affinity for the AMPA receptors. Because of their action profile, the compounds according to the invention are suitable for the treatment of diseases that are caused by hyperactivity of excitatory amino acids, such as, for example, glutamate or aspartate. Since the new compounds act as antagonists of excitatory amino acids and show a high specific affinity for the AMPA receptors, in which they displace the radiolabeled specific agonist (RS)α-amino-3-hydroxy-5-methyl-4-isoxazolepropionate (AMPA) from the AMPA receptors, they are especially suitable for the treatment of those diseases that are affected by the receptors of excitatory amino acids, especially the AMPA receptor.

According to the invention, the compounds can be used for the treatment of neurological and psychiatric disorders that are triggered by the overstimulation of the AMPA receptor. The neurological diseases that can be treated functionally and preventatively include, for example, neurodegenerative disorders, such as Parkinson's disease, Alzheimer's disease, Huntington chorea, amyotrophic lateral sclerosis and olivopontocerebellar degeneration. According to the invention, the compounds can be used for the prevention of postischemic cell destruction, cell destruction after cerebral trauma, in a stroke, hypoxia, anoxia and hypoglycemia and for treatment of senile dementia, AIDS dementia, neurological symptoms that are linked with HIV infections, multiinfarct dementia as well as epilepsy and muscle spasms. The psychiatric diseases include anxiety conditions, schizophrenia, migraine, conditions of pain, as well as the treatment of sleep disorders and the withdrawal symptoms after drug abuse, such as in alcohol, cocaine, benzodiazepine or opiate withdrawal. In addition, the compounds can be used in the prevention of tolerance development during long-term treatment with sedative pharmaceutical agents, such as, for example, benzodiazepines, barbiturates and morphine. Moreover, the compounds can be used as anesthetic agents (anesthesia), anti-analgesics or anti-emetics.

For use of the compounds according to the invention as pharmaceutical agents, they are put in the form of a pharmaceutical preparation, that, besides the active ingredient for enteral or parenteral administration, contains suitable pharmaceutical, organic or inorganic inert vehicles, such as, for example, water, gelatin, gum arabic, lactose, starch, magnesium stearate, talc, vegetable oils, polyalkyleneglycols, etc. The pharmaceutical preparations can be in solid form, for example, as tablets, coated tablets, suppositories, capsules or in liquid form, for example, as solutions, suspensions or emulsions. Moreover, they optionally contain adjuvants, such as preservatives, stabilizers, wetting agents or emulsifiers, salts for changing the osmotic pressure or buffers.

Especially suitable for parenteral use are injection solutions or suspensions, in particular aqueous solutions of the active compounds in polyhydroxy-ethoxylated castor oil. Surface-active adjuvants, such as salts of bile acids or animal or vegetable phospholipids, but also mixtures thereof as well as liposomes or their components can also be used as vehicle systems.

Especially suitable for oral use are tablets, coated tablets or capsules with talc and/or hydrocarbon vehicles or binders, such as, for example, lactose, cor or potato starch. The use can even be carried out in liquid form, such as, for example, as juice, to which a sweetner is optionally added.

The dosage of the active ingredients can vary depending on method of administration, age and weight of the patient, type and severity of the disease to be treated and similar factors, the daily dose is 0.5–1000 mg, preferably 50–200 mg, whereby the dose can be administered as a single dose to be administered once or subdivided into 2 or more daily doses.

The production of the compounds according to the invention is carried out according to methods known in the art. For example, compounds of formula I are attained in that a) a compound of formula II

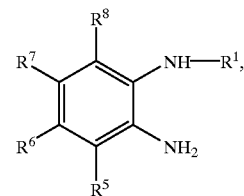

(II)

in which $R^1$ and $R^8$ have the above-mentioned meaning, is cyclized with oxalic acid or reactive oxalic acid derivatives or b) a compound of formula III

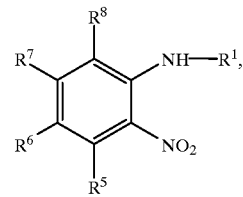

(III)

in which $R^1$ and $R^8$ have the above-mentioned meaning, is reacted with oxalic acid or reactive oxalic acid derivatives and is cyclized after reduction of the nitro group, or c) a compound of formula IV

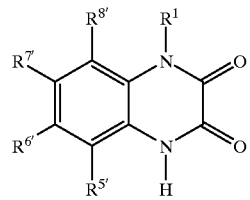

(IV)

in which $R^1$ has the above-mentioned meaning and one of substituents $R^{5'}$, $R^{6'}$, $R^{7'}$, or $R^{8'}$, represents a leaving group, is nucleophilically substituted and then optionally the ester group is saponified or the acid group is esterified or amidated or a hydroxy group is etherified or a nitrile is converted into tetrazole or the isomers are separated or the salts are formed.

The cyclization to compounds of formula I is carried out single-stage with oxalic acid in a known way in an acid environment or single-stage with a reactive oxalic acid derivative or else two-stage. Regarded as preferable is the two-stage process in which the diamine is reacted with an oxalic acid derivative such as oxalic ester semi-chloride or other reactive oxalic acid derivatives such as mixed anhydride, activated ester, imidazolides in polar solvents, such as cyclic or acyclic ethers or halogenated hydrocarbons, for example, tetrahydrofuran, diethyl ether or methylene chloride in the presence of a base such as organic amines, for example, triethylamine, pyridine, Hünig base or dimethylaminopyridine. Hydroxides such as, e.g., solid sodium or potassium hydroxide or carbonates, such as, e.g., sodium carbonate in polar solvents, such as, e.g., tetrahydrofuran, or else alkali hydrides such as NaH, which are used in inert solvents, such as hydrocarbons or ethers, represent suitable bases for the two-stage process.

The subsequent cyclization can be performed in a basic or else acidic manner, but preferably in an acid environment, whereby alcohol can be added to the reaction mixture as solubilizer.

In process variant b), after acylation with oxalic acid or the reactive oxalic acid derivative, the nitro group is catalytic or is reduced to alcohol in the usual way by reduction with iron powder in acetic acid at a higher temperature or else with sodium sulfide and ammonium hydroxide and cyclized as described above.

As leaving groups in process variant c), as well as in the production of starting compounds of formula II, halogens such as fluorine, chlorine, bromine, iodine or O-derivatives such as O-mesylate, O-tosylate, O-triflate or O-nonaflate are suitable. The nucleophilic substitution is performed according to methods known in the literature in the presence of a base and is fostered by one or more activating electron-attracting groups, such as, e.g., nitro, cyano, trifluoromethyl, preferably in o- or p-position.

As nucleophiles, for example, alcoholates, thiols or primary as well as secondary amines, or else water, are suitable. The reaction can be performed in polar solvents such as alcohols, halogenated hydrocarbons, dimethylacetamide, acetonitrile or water or without solvents. As bases, inorganic bases, such as alkali or alkaline-earth hydroxides or carbonates, or organic bases, such as cyclic, acyclic and aromatic amines, such as DBU, Hünig base, pyridine or dimethylaminopyridine, are suitable.

In the case of amines, the nucleophile itself is used in excess as base, whereby optionally it is possible to work without additional solvent. In the case of amine having too low a boiling point, the reaction can optionally be performed under pressure in an autoclave.

The optionally subsequent saponification of an ester group can be carried out in a basic or preferably acidic manner, by hydrolyzing the reaction mixture at a higher temperature up to the boiling temperature in the presence of acids, such as highly concentrated aqueous hydrochloric acid optionally in solvents, such as, for example, trifluoroacetic acid or alcohols. Phosphonic acid esters are preferably hydrolyzed by heating in highly concentrated aqueous acids, such as, for example, concentrated hydrochloric acid optionally with addition of an alcohol or by treatment with a trimethylsilyl halide in inert solvents, such as, e.g., acetonitrile and subsequent treatment with water.

The esterification of the carboxylic acid or phosphonic acid is carried out in a way known in the art with the corresponding alcohol optionally by acid catalysis or by using an activated acid derivative. As activated acid derivatives, for example, acid chloride, acid imidazolide or acid anhydride are suitable. In all acids, but especially the phosphonic acids, the esterification can be achieved by reaction with orthoesters optionally by addition of catalysts such as p-toluenesulfonic acid.

The amidation is carried out on the free acids or on their reactive derivatives, such as, for example, acid chlorides, mixed anhydrides, imidazolides or azides, by reaction with the corresponding amines at room temperature.

The reduction of the nitro group to an amino group is carried out catalytically in polar solvents at room temperature or a higher temperature. As catalysts, metals such as Raney nickel or noble metal catalysts such as palladium or platinum, optionally on vehicles, are suitable. Instead of hydrogen, ammonium formate can also be used in a known way. Reducing agents such as tin(II)chloride or titanium(III) chloride can be used just as complex metal hydrides possibly in the presence of heavy metal salts. Iron can also be used as a reducing agent. The reaction is then performed in the presence of an acid, such as, e.g., acetic acid or ammonium chloride, optionally by addition of a solvent such as water. It can be advantageous to introduce the ester group before the reduction. In the presence of several nitro groups in the molecule, the desired nitro group in ortho position can also be selectively reduced with $Na_2S$ in the usual way.

The phenolic function can be etherified by, for example, reaction with an alkyl halide, -tosylate, -triflate or the like in the presence of bases, such as, e.g., alkaline-earth or alkali hydroxides or carbonates in polar solvents, such as, e.g., DMF, THF or methylene chloride or according to the Mitsonubo variant by reaction with an alcohol in the presence of a phosphine, such as, e.g., triphenylphosphine and azodicarboxylic acid ester or amide.

The introduction of an $NO_2$ group is possible by a series of known nitration methods. For example, nitration can be performed with nitronium tetrafluoroborate in inert solvents, such as halogenated hydrocarbons or in sulfolane, glacial acetic acid or acetonitrile. The introduction is also possible by, e.g., nitrating acid in concentrated sulfuric acid or nitrates, such as, e.g., $KNO_3$ in trifluoroacetic acid as solvent, at temperatures of between 0° C. and 30° C.

The introduction of halogen is possible by known halogenation methods, such as by, e.g., electrophilic aromatic substitution.

For example, iodization can be performed according to a process with iodine and iodic acid of Wirth et al. [*Liebigs Ann. Chem.* 634, 84 (1960)] or with N-iodosuccinidime in solvents such as tetrahydrofuran, dimethylformamide or trifluoromethanesulfonic acid.

The introduction of the tetrazole is possible by reaction of the corresponding nitrile with an azide, such as, e.g., trimethylsilylazide, hydrazoic acid or sodium azide, optionally by addition of a proton source such as, e.g, ammonium chloride or triethylammonium chloride in polar solvents such as dimethylformamide, dimethylacetamide or N-methylpyrrolidine at temperatures up to the boiling point of the solvent.

The mixture of isomers can be separated into the enantiomers or E/Z isomers according to commonly used methods, such as, for example, crystallization, chromatography or salt formation.

The production of the salts is carried out in the usual way, by a solution of the compound of formula I being mixed with the equivalent amount or excess base or acid, which optionally is in solution, and the precipitate being separated or the solution being worked up in the usual way.

If the production of the starting compounds is not described, they are known or can be produced analogously to known compounds, for example, according to WO93/08173, or according to processes described here.

The following examples are to explain the process according to the invention:

Production of starting compounds

1.) 3.2 g of N-(2-nitro-4-trifluoromethyl-5-fluorophenyl)-aminemethanephosphonic acid is stirred in 40 ml of 2N potassium hydroxide solution for 36 hours at room temperature. The starting material has then virtually disappeared. It is acidified with 4N hydrochloric acid to pH 1 and shaken three times with 80 ml of ethyl acetate each. The ethyl acetate phase is washed with 80 ml of concentrated common salt solution, dried, filtered and concentrated by evaporation. After the residue is absorptively precipitated with ethyl acetate, 2.29 g of N-(2-nitro-4-trifluoromethyl-5-hydroxyphenyl)-aminomethanephosphonic acid is obtained.

2.) 2.29 g of N-(2-nitro-4-trifluoromethyl-5-hydroxyphenyl)-aminemethanephosphonic acid is heated to 120° C. in 28 ml of triethyl orthoformate under argon and with exclusion of moisture for 1 hour in a water separator. Then, it is concentrated by evaporation and chromatographed on silica gel with methylene chloride:ethanol=95.5. 1.9 g or N-(2-nitro-4-trifluoromethyl-5-hydroxy-phenyl)-aminomethanephosphonic acid diethyl ester is obtained.

3.) 930 mg of N-(2-nitro-4-trifluoromethyl-5-hydroxyphenyl)-aminomethanephosphonic acid diethyl ester is dissolved with 860 mg of 2-(4-chlorophenoxy)ethanol and 1.31 g of triphenylphosphine, 25 ml of tetrahydrofuran, mixed with 870 mg (0.8 ml) of azodicarboxylic acid diethyl ester and heated for 0.25 hour to 80° C. in a preheated oil bath. After concentration by evaporation in a vacuum, the residue is chromatographed on silica gel with methylene chloride:ethanol=95.5. The fractions that are combined in a corresponding way contain N-[2-nitro-4-trifluoromethyl-5-(2(4-chlorophenoxy)ethoxy)phenyl]-aminomethanephosphonic acid diethyl ester that is contaminated with triphenylphosphine oxide, and they are used without additional purification in the next step.

Produced analogously are:

N-[2-Nitro-4-trifluoromethyl-5-(N-[4(-4-fluorobenzoyl)piperidin-1-yl)]propyloxyphenyl]-aminomethanephosphonic acid diethyl ester N-[2-nitro-4-trifluoromethyl-5-(2-diethylaminoethoxy)phenyl)]-aminomethanephosphonic acid diethyl ester 4.) 3.18 g of N-(2-nitro-4-trifluoromethyl-5-fluorophenyl)-aminomethanephosphonic acid is stirred together with 3.18 g of sodium carbonate and 2.82 g of phenol in 40 ml of water for 4 hours at a bath temperature of 120° C. After acidification with 4N hydrochloric acid, the precipitated product is suctioned off. 2.69 g of N-(2-nitro-4-trifluoromethyl-5-phenoxyphenyl)-aminomethanephosphonic acid is obtained.

Produced analogously are:

N-(2-Nitro-4-trifluoromethyl-5-(4-methoxyphenoxy)phenyl)-aminomethanephosphonic acid N-(2-nitro-4-trifluoromethyl-5-(4-chlorophenoxy)phenyl)-aminomethanephosphonic acid N-(2-nitro-4-trifluoromethyl-5-(3-trifluoromethylphenoxy)phenyl)-aminomethanephosphonic acid N-(2-nitro-4-trifluoromethyl-5-(4-hydroxycarbonylphenoxy)phenyl)-aminomethanephosphonic acid (from 4-trifluoromethylphenol)

N-(2-nitro-4-trifluoromethyl-5-(hexafluoroisopropoxyphenyl)-aminomethanephosphonic acid N-(2-nitro-4-trifluoromethyl-5-(pentafluoropropoxyphenyl)-aminomethanephosphonic acid N-(2-nitro-4-trifluoromethyl-5-(heptafluorobutoxyphenyl)-aminomethanephosphonic acid N-(2-nitro-4-trifluoromethyl-5-(butoxycarbonylmethyloxyphenyl-aminomethanephosphonic acid 5.) An ethyl acetate solution of 3.18 g of N-(2-nitro-4-trifluoromethyl-5-fluorophenyl)-aminomethanephosphonic acid is mixed with 30 ml of benzyl alcohol, and the ethyl acetate is distilled off. 60 ml of 1N sodium hydroxide solution is added, and it is stirred for 1.25 hours at a bath temperature of 120° C. Then, 30 ml of 1N sodium hydroxide solution is added again, and it is stirred for another 0.75 hour at 120° C. After cooling, it is extracted twice with 100 ml of ethyl acetate each. The ethyl acetate phase is discarded. The aqueous phase is acidified to pH 1 with 4N hydrochloric acid and extracted three times with 100 ml of ethyl acetate each. This collected ethyl acetate phase is washed once with water, dried, filtered and concentrated by evaporation. The residue contains N-[2-nitro-4-trifluoromethyl-5-benzyloxyphenyl]-aminomethanephosphonic acid and is further reacted without additional purification.

Produced analogously is:

N-[2-Nitro-4-trifluoromethyl-5-((-3,6-dioxahept-1-yl)oxy)phenyl]-aminomethanephosphonic acid 6.) 2.5 g of N-(2-nitro-4-trifluoromethyl-5-phenoxyphenyl)-aminomethanephosphonic acid is heated in 19 ml of triethyl orthoformate with 184 mg of p-toluenesulfonic acid for 3.75 hours to 120° C. in a water separator. After concentration by evaporation in a vacuum, the residue is chromatographed on silica gel with methylene chloride:ethanol=10:2. 2.71 g of N-(2-nitro-4-trifluoromethyl-5-phenoxyphenyl)-aminomethanephosphonic acid diethyl ester, which is used without additional purification in the next step, is obtained.

Produced analogously are:

N-(2-Nitro-4-trifluoromethyl-5-(4-methoxyphenoxyl)phenyl)-aminomethanephosphonic acid dietyl ester N-(2-nitro-4-trifluoromethyl-5-(4-chlorophenoxy)phenyl)-aminomethanephosphonic acid dietyl ester N-(2-nitro-4-trifluoromethyl-5-(3-trifluoromethylphenoxy)-phenyl)-aminomethanephosphonic acid diethyl ester N-(2-nitro-4-trifluoromethyl-5-(4-ethoxycarbonylphenoxy)phenyl)-aminomethanephosphonic acid diethyl ester N-(2-nitro-4-trifluoromethyl-5-(hexafluoroisopropoxyphenyl)-aminomethanephosphonic acid diethyl ester N-(2-nitro-4-trifluoromethyl-5-(pentafluoropropoxyphenyl)-aminomethanephosphonic acid diethyl ester N-(2-nitro-4-trifluoromethyl-5-(heptafluorobutoxyphenyl)-aminomethanephosphonic acid diethyl ester N-[2-nitro-4-trifluoromethyl-5-benzyloxyphenyl]-aminomethanephosphonic acid diethyl ester N-[2-nitro-4-trifluoromethyl-5-((-3,6-dioxahept-1-yl)oxy)phenyl]-aminomethanephosphonic acid diethyl ester N-[2-nitro-4-trifluoromethyl-5-(butoxycarbonylmethyloxy)-phenyl] aminomethanephosphonic acid diethyl ester 7.) 2.5 g of unpurified N-[2-nitro-4-trifluoromethyl-5-(2(-4-chlorophenoxy)ethoxy)phenyl]-aminomethanephosphonic acid diethyl ester is dissolved in 27 ml of methanol and added quickly under nitrogen to a mixture of 658 mg of ammonium chloride and 419 mg of iron powder in 13 ml of water. Then, it is heated for 0.5 hour to 80° C. After diatomaceous earth is suctioned out and it is rewashed with warm methanol, the filtrate is diluted with water to 75 ml and extracted three times with 50 ml of ethyl acetate each. The ethyl acetate phase is washed with water, dried, filtered and concentrated by evaporation. 2.5 g of N-[2-amino-4-trifluoromethyl-5-(2(-4-chlorophenoxy)ethoxy-phenyl]-aminomethanephosphonic acid diethyl ester that is also contaminated with triphenylphosphine and that is further reacted without additional purification is obtained.

Produced analogously are:

N-[2-Amino-4-trifluoromethyl-5-((-3,6-dioxahept-1-yl)oxy)phenyl]-aminomethanephosphonic acid diethyl ester N-[2-amino-4-trifluoromethyl-5-benzyloxyphenyl]-aminomethanephosphonic acid diethyl ester N-[2-amino-4-trifluoromethyl-5-((N-4(-4-fluorobenzoyl)piperidin-1-yl))propyloxyphenyl]-aminomethanephosphonic acid diethyl ester 8.) N-(2-Nitro-4-trifluoromethyl-5-phenoxyphenyl)-aminomethanephosphonic acid diethyl ester is mixed in 100 ml of ethanol with 1 g of palladium on carbon (10%) and hydrogenated under hydrogen atmosphere at room temperature and normal pressure for 2 hours. After catalyst is suctioned out on diatomaceous earth and after concentration by evaporation in a vacuum, 2.6 g of N-(2-amino-4-trifluoromethyl-5-phenoxyphenyl)-aminomethanephosphonic acid diethyl ester, which is used without additional purification in the next step, is obtained.

Produced analogously are:

N-(2-Amino-4-trifluoromethyl-5-(4-methoxyphenyl)phenyl)-aminomethanephosphonic acid diethyl ester N-(2-amino-4-triflurormethyl-5-(4-chlorophenoxy)phenyl)-aminomethanephosphonic acid diethyl ester N-(2-amino-4-trifluoromethyl-5-(3-trifluoromethylphenoxy)phenyl)-aminomethanephosphonic acid diethyl ester N-(2-amino-4-trifluoromethyl-5-(4-ethoxycarbonylphenoxy)phenyl)-aminomethanephosphonic acid diethyl ester N-(2-amino-4-trifluoromethyl-5-(hexafluoroisopropoxyphenyl)-aminomethanephosphonic acid diethyl ester N-(2-amino-4-trifluoromethyl-5-(pentafluoropropoxyphenyl)-aminomethanephosphonic acid diethyl ester N-(2-amino-4-trifluoromethyl-5-(heptafluorobutoxyphenyl)-aminomethanephosphonic acid diethyl ester N-[2-amino-4-trifluoromethyl-5-(2-diethylaminoethoxy)phenyl]-aminomethanephosphonic acid diethyl ester N-[2-amino-4-trifluoromethyl-5-(butoxycarbonylmethyloxy]-aminomethanephosphonic acid diethyl ester

Example 1

2.5 g of N-[2-amino-4-trifluoromethyl-5-(2(-4-chlorophenoxy)ethoxy)phenyl]-aminomethanephosphonic acid diethyl ester is introduced in 60 ml of tetrahydrofuran with 733 mg of triethylamine and mixed drop by drop at room temperature with a solution of 719 mg (0.59 ml) of oxalic acid ethyl ester chloride in 15 ml of tetrahydrofuran. Then, it is stirred for 2 hours at room temperature. After triethylammonium hydrochloride is suctioned out, the filtrate is concentrated by evaporation. The residue is taken up in 25 ml of ethanol and 25 ml of 1N hydrochloric acid and heated for 2 hours to a bath temperature of 120° C. After the ethanol is distilled off, it is diluted with water to 50 ml, and extracted three times with 50 ml of ethyl acetate each. The ethyl acetate phase is washed with water, dried, filtered and concentrated by evaporation. The residue is chromatographed on silica gel with methylene chloride:ethanol=10:1. 810 mg of [(6-trifluoromethyl-7-(2(-4-chlorophenoxy)ethoxy)-1,2,3,4-tetrahydro-2,3-dioxoquinoxalin-1-yl]methanephosphonic acid diethyl ester is obtained.

Produced analogously are:

[(6-Trifluoromethyl-7-(-3,6-dioxahept-1-yl)oxy)-1,2,3,4-tetrahydro-2,3-dioxoquinoxalin)-1-yl]-methanephosphonic acid diethyl ester

[(6-trifluoromethyl-7-(4-methoxyphenoxy)-1,2,3,4-tetrahydro-2,3-dioxoquinoxalin)-1-yl]-methanephosphonic acid diethyl ester

[(6-trifluoromethyl-7-benzyloxy-1,2,3,4-tetrahydro-2,3-dioxoquinoxalin)-1-yl]-methanephosphonic acid diethyl ester

[(6-trifluoromethyl-7-phenoxy-1,2,3,4-tetrahydro-2,3-dioxoquinoxalin)-1-yl]-methanephosphonic acid diethyl ester

[(6-trifluoromethyl-7-(4-chlorophenoxy)-1,2,3,4-tetrahydro-2,3-dioxoquinoxalin)-1-yl]-methanephosphonic acid diethyl ester with a melting point

[(6-trifluoromethyl-7-(3-trifluoromethylphenoxy)-1,2,3,4-tetrahydro-2,3-dioxoquinoxalin)-1-yl]-methanephosphonic acid diethyl ester

[(6-trifluoromethyl-7-hexafluoroisopropoxy-1,2,3,4-tetrahydro-2,3-dioxoquinoxalin)-1-yl]-methanephosphonic acid diethyl ester

[(6-trifluoromethyl-7-pentafluoropropoxy-1,2,3,4-tetrahydro-2,3-dioxoquinoxalin)-1-yl]-methanephosphonic acid diethyl ester

[(6-trifluoromethyl-7-heptafluorobutoxy-1,2,3,4-tetrahydro-2,3-dioxoquinoxalin)-1-yl]-methanephosphonic acid diethyl ester

[(6-trifluoromethyl-7-(4-ethoxycarbonylphenoxy)-1,2,3,4-tetrahydro-2,3-dioxoquinoxalin)-1-yl]-methanephosphonic acid diethyl ester

[(6-trifluoromethyl-7-(2-diethylaminoethoxy)-1,2,3,4-tetrahydro-2,3-dioxoquinoxalin)-1-yl]-methanephosphonic acid diethyl ester

[(6-trifluoromethyl-7-(N-4(-4-fluorobenzyl)piperidin-1-yl))propyloxy)-1,2,3,4-tetrahydro-2,3-dioxoquinoxalin)-1-yl]-methanephosphonic acid diethyl ester

[(6-trifluoromethyl-7-(hydroxycarbonylmethyloxy)-1,2,3,4-tetrahydro-2,3-dioxoquinoxalin-1yl]-methanephosphonic acid diethyl ester

Example 2

750 mg of [(6-trifluoromethyl-7-(2(-4-chlorophenoxy)ethoxy)-1,2,3,4-tetrahydro-2,3-dioxoquinoxalin)-1-yl]-methanephosphonic acid diethyl ester is mixed in 36 ml of acetonitrile with 1.73 g (1.46 ml) of trimethylbromsilane, and it is stirred for 1.5 hours at room temperature and then at 80° C. A little water is then added, and it is stirred at room temperature for 15 minutes. Then, it is concentrated by evaporation in a vacuum, and the residue is absorptively precipitated with water and suctioned off. 650 mg of [(6-trifluoromethyl-7-(2(-4chlorophenoxy)ethoxy)-1,2,3,4-tetrahydro-2,3-dioxoquinoxalin)-1-yl]-methanephosphonic acid with a melting point of 250° C. is obtained.

Produced analogously are:

[(6-Trifluoromethyl-7-(3,6-dioxahept-1-yl)oxy)-1,2,3,4-tetrahydro-2,3-dioxoquinoxalin)-1-yl]methanephosphonic acid (in this case, [(6-trifluoromethyl-7-(3,6-dioxahex-1-yl)-1,2,3,4-tetrahydro-2,3-dioxoquinoxalin)-1-yl]-methanephosphonic acid is produced as a by-product)

[(6-trifluoromethyl-7-(4-methoxyphenoxy)-1,2,3,4-tetrahydro-2,3-dioxoquinoxalin)-1-yl]-methanephosphonic acid with a melting point >300° C.

[(6-trifluoromethyl-7-benzyloxy-1,2,3,4-tetrahydro-2,3-dioxoquinoxalin)-1-yl]-methanephosphonic acid with a melting point >300° C.

[(6-trifluoromethyl-7-(N-4(-4-fluorobenzoyl)piperidin-1-yl))propyloxy)-1,2,3,4-tetrahydro-2,3-dioxoquinoxalin)-1-yl]-methanephosphonic acid with a melting point of 233.5° C.

[(6-trifluoromethyl-7-(hydroxycarbonylmethyloxy)-1,2,3,4-tetrahydro-2,3-dioxoquinoxalin)-1-yl]-methanephosphonic acid Example 3

256 mg of [(6-trifluoromethyl-7-phenoxy-1,2,3,4-tetrahydro-2,3-dioxoquinoxalin)-1-yl]-methanephosphonic acid diethyl ester is heater to 120° C. in 4 ml of concentrated hydrochloric acid for 2 hours. The batch is diluted with water, and the precipitated product is suctioned off. 207 mg of [(6-trifluoromethyl-7-phenoxy-1,2,3,4-tetrahydro-2,3-dioxoquinoxalin)-1-yl]-methanephosphonic acid with a melting point >300° C. is obtained.

Produced analogously are:

[(6-Trifluoromethyl-7-(4-chlorophenoxy)-1,2,3,4-tetrahydro-2,3-dioxoquinoxalin)-1-yl]-methanephosphonic acid with a melting point >300° C.

[(6-trifluoromethyl-7-(3-trifluoromethylphenoxy)-1,2,3,4-tetrahydro-2,3-dioxoquinoxalin)-1-yl]-methanephosphonic acid with a melting point of 222° C.

[(6-trifluoromethyl-7-benzyloxy-1,2,3,4-tetrahydro-2,3-dioxoquinoxalin)-1-yl]-methanephosphonic acid with a melting point >300° C.

[(6-trifluoromethyl-7-hexafluoroisopropoxy-1,2,3,4-tetrahydro-2,3-dioxoquinoxalin)-1-yl]-methanephosphonic acid with a melting point of 280° C.

[(6-trifluoromethyl-7-pentafluoropropoxy-1,2,3,4-tetrahydro-2,3-dioxoquinoxalin)-1-yl]-methanephosphonic acid with a melting point of 239.2° C.

[(6-trifluoromethyl-7-heptafluorobutoxy-1,2,3,4-tetrahydro-2,3-dioxoquinoxalin)-1-yl]-methanephosphonic acid with a melting point of 161.9° C.

[(6-trifluoromethyl-7-(4-hydroxycarbonylphenoxy)-1,2,3,4-tetrahydro-2,3-dioxoquinoxalin)-1-yl]-methanephosphonic acid with a melting point >300° C.

[(6-trifluoromethyl-7-(2-diethylaminoethoxy)-1,2,3,4-tetrahydro-2,3-dioxoquinoxalin)-1-yl]-methanephosphonic acid with a melting point >300° C.

What is claimed is:

1. A compound of formula I

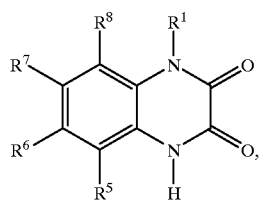

(I)

wherein
$R^1$ is —$(CH_2)_n$—$CR^2H$—$(CH_2)_m$—Z
$R^5, R^6, R^7$ and $R^8$ are the same or different and are hydrogen; $C_{1-6}$ alkyl, in which optionally one or more hydrogen atoms are replaced by halogen atoms; nitro; halogen; $NR^9R^{10}$; $SO_pR^{11}$; $SO_2NR^{12}R^{13}$; $SO_3H$; $SO_3C_{1-6}$-alkyl or $OR^{14}$,
$R^2$ is hydrogen or —$(CH_2)_q$—$R^3$,
$R^3$ is hydrogen, hydroxy, $C_{1-6}$-alkoxy or $NR^{15}R^{16}$, n, m and q each are 0, 1, 2 or 3,
Z is POXY, OPOXY, $SO_2R^{17}$, $CO_2R^{18}$, halogen, cyano or tetrazole,
$R^{11}$ is H, $C_{1-6}$-alkyl or phenyl,
p is 0, 1, or 2,
$R^{12}$ and $R^{13}$, independently of one another, are hydrogen or $C_{1-4}$-alkyl,
$R^{14}$ is A—$R^{19}$ or a $C_{6-12}$-aryl or 5- or 6-membered hetaryl radical having 1–3 N, O and/or S atoms, optionally substituted with halogen $C_{1-6}$-alkoxy, hydroxy, cyano, $NR^{20}R^{21}$, $C_{1-6}$-alkyl optionally substituted with halogen, and/or $COR^{22}$,
A is straight-chain or branched, saturated or unsaturated $C_{1-10}$-alkylene, wherein one or more carbon atoms is optionally replaced by O, S and/or $NR^{26}$ and optionally substituted in one or more places with halogen,
$R^{19}$ is hydrogen; $NR^{24}R^{25}$; halogen; $C_{1-6}$-alkyl, optionally substituted in one or more places with halogen; $C_{1-6}$-alkoxy; $COR^{23}$; CN or a $C_{6-12}$-aryl or 5- or 6-membered hetaryl radical having 1–3 N, O and/or S atoms, optionally substituted with halogen, $C_{1-6}$-alkoxy, hydroxy, cyano, $NR^{20}R^{21}$, $C_{1-6}$-alkyl optionally substituted with halogen, and/or $COR^{22}$,
$R^{18}$ is hydrogen, $C_{1-4}$-alkyl, hydroxy, $C_{1-6}$-alkoxy or $NR^{27}R^{28}$,
$R^{17}$, $R^{22}$ and $R^{23}$ are hydroxy, $C_{1-6}$ alkoxy or $NR^{29}R^{30}$,
$R^{26}$ is hydrogen, $C_{1-4}$-alkyl or $C_{1-6}$-alkanoyl,
X and Y are the same or different and are hydroxy, $C_{1-6}$-alkoxy, $C_{1-4}$-alkyl or $NR^{27}R^{28}$,
$R^9$ and $R^{10}$, $R^{20}$ and $R^{21}$ and or $R^{25}$ and $R^{24}$ are the same or different and are hydrogen; CO—$C_{1-6}$-alkyl, phenyl or $C_{1-6}$-alkyl, optionally substituted with $C_{1-4}$-alkoxy or an amino group optionally mono- or disubstituted with $C_{1-4}$-alkyl; or together with the nitrogen atom form a saturated 5- or 7-membered saturated heterocycle optionally having another N, S or O atom and optionally substituted 1–3 times with $C_{1-4}$-alkyl or a phenyl, benzyl or benzoyl radical optionally substituted by halogen, or form an unsaturated 5-membered heterocycle having 1–3 N atoms and optionally substituted once or twice with cyano, $C_{1-4}$-alkyl, phenyl or CO—$C_{1-6}$-alkyl,
$R^{15}$ and $R^{16}$, $R^{27}$ and $R^{28}$ and/or $R^{29}$ and $R^{30}$ are the same or different and are hydrogen, $C_{1-4}$-alkyl, phenyl or together with the nitrogen atom form a saturated 5- or 7-membered saturated heterocycle optionally having another oxygen, sulfur or nitrogen atom and optionally substituted 1–3 times with $C_{1-4}$-alkyl or a phenyl, benzyl or benzoyl radical optionally substituted by halogen, or form an unsaturated 5-membered heterocycle optionally having 1–3 N atoms and optionally substituted once or twice with cyano, $C_{1-4}$-alkyl, phenyl or $CO_2C_{1-6}$-alkyl,
with the provisos that
one of the radicals $R^5$–$R^8$ always is $OR^{14}$, and $R^{14}$ does not mean H or $C_{1-6}$-alkyl optionally substituted in 1–3 places with halogens, and
if Z is $CO_2R^{18}$ and one of the radicals $R^5$–$R^8$ is $OR^{14}$, at least one other radical $R^5$–$R^8$ is $C_{1-4}$-alkyl substituted by halogen.

2. A compound of claim 1, wherein Z is POXY.
3. A compound of claim 1, wherein Z is OPOXY.
4. A compound of claim 1, wherein
$R^5, R^6, R^7$ and $R^8$ are the same or different and are hydrogen; $C_{1-6}$ alkyl, in which optionally one or more hydrogen atoms are replaced by halogen atoms; nitro; cyano; or $OR^{14}$, $R^3$ is hydrogen, and Z is POXY or $CO_2R^{18}$.

5. [(6-Trifluoromethyl-7-(2-(4-chlorophenoxy(ethoxy)-1,2,3,4-tetrahydro-2,3-dioxoquinoxalin)-1-yl]-methanephosphonic acid

[(6-trifluoromethyl_7-phenoxy-1,2,3,4-tetrahydro-2,3-dioxoquinoxalin)-1-yl]methanephosphonic acid

[(6-trifluoromethyl-7-(-3,6-dioxahept-1-yl)oxy)-1,2,3,4-tetrahydro-2,3-dioxoquinoxalin)-1-yl]-methanephosphonic acid

[(6-trifluoromethyl-7-(4-methoxyphenoxy)-1,2,3,4-tetrahydro-2,3-dioxoquinoxalin)-1-yl]methanephosphonic acid

[(6-trifluoromethyl-7-benzyloxy-1,2,3,4-tetrahydro-2,3-dioxoquinoxalin)-1-yl]-methanephosphonic acid

[(6-trifluoromethyl-7-(N-4(-4-fluorobenzoyl)piperidin-1-yl))propyloxy)-1,2,3,4-tetrahydo-2,3-dioxoquinoxalin)-1-yl]-methanephosphonic acid

[(6-trifluoromethyl-7-(hydroxycarbonylmethyloxy)-1,2,3,4-tetrahydro-2,3-dioxoquinoxalin)-1-yl]-methanephosphonic acid

[(6-trifluoromethyl-7-(4-chlorophenoxy)-1,2,3,4-tetrahydro-2,3-dioxoquinoxalin)-1-yl]-methanephosphonic acid

[(6-trifluoromethyl-7-(3-trifluoromethylphenoxy)-1,2,3,4-tetrahydro-2,3-dioxoquinoxalin(-1-yl]-methanephosphonic acid

[(6-trifluoromethyl-7-(4-hydroxycarbonylphenoxy)-1,2,3,4-tetrahydro-2,3-dioxoquinoxalin)-1-yl]-methanephosphonic acid

[(6-trifluoromethyl-7-(2-diethylaminoethoxy)-1,2,3,4-tetrahydro-2,3-dioxoquinoxalin)-1-yl]-methanephosphonic acid.

6. A process for the production of a compound of formula I of claim 1, comprising a) cyclizing a compound of formula II (II)

wherein $R^1$ and $R^5$–$R^8$ have the meaning as defined in claim 1, with oxalic acid or a reactive oxalic acid derivative, or b) reacting a compound of formula III (III)

wherein $R^1$ and $R^5$–$R^8$ have the meaning as defined in claim 1, with oxalic acid or a reactive oxalic acid derivative and cyclizing after reduction of the nitro group, or c) nucleophilically substituting a compound of formula IV (IV)

wherein $R^1$ has the meaning as defined in claim 1 and one of the substituents $R^{5'}$, $R^{6'}$, $R^{7'}$ or $R^{8'}$ represents a leaving group which corresponds to $R^5$, $R^6$, $R^7$ or $R^8$, respectively, as defined in claim 1, and then optionally saponifying an ester group, or esterifying or amidating an acid group, or etherifying a hydroxy group, or converting a nitrile group into a tetrazole group, or separating tautomers, enantiomers or E/Z isomers, or forming a salt of the compound of formula I.

7. A pharmaceutical composition comprising an effective amount of a compound of claim 1 and a pharmaceutically acceptable excipient.

8. A method of treating Parkinson's disease, Alzheimer's disease, Huntington's chorea, amyotrophic lateral sclerosis and olivopontocerebellar degeneration, comprising administering to a patient in need of such treatment an effective amount of a compound of claim 1.

* * * * *